(12) United States Patent
Peck et al.

(10) Patent No.: US 9,045,794 B2
(45) Date of Patent: Jun. 2, 2015

(54) COMPOSITIONS AND METHODS FOR MONITORING OXALATE

(75) Inventors: Ammon B. Peck, Gainesville, FL (US); Cuong Q. Nguyen, Gainesville, FL (US); Nigel G. John Richards, Indianapolis, IN (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/984,251

(22) PCT Filed: Feb. 7, 2012

(86) PCT No.: PCT/US2012/024164
§ 371 (c)(1),
(2), (4) Date: Aug. 26, 2013

(87) PCT Pub. No.: WO2012/109258
PCT Pub. Date: Aug. 16, 2012

(65) Prior Publication Data
US 2013/0330760 A1     Dec. 12, 2013

Related U.S. Application Data

(60) Provisional application No. 61/440,133, filed on Feb. 7, 2011.

(51) Int. Cl.
C12Q 1/26     (2006.01)
C12Q 1/28     (2006.01)
C12Q 1/527    (2006.01)
G01N 33/52    (2006.01)

(52) U.S. Cl.
CPC *C12Q 1/527* (2013.01); *C12Q 1/26* (2013.01); *C12Q 1/28* (2013.01); *G01N 33/523* (2013.01); *G01N 2800/347* (2013.01)

(58) Field of Classification Search
None
See application file for complete search history.

(56) References Cited

U.S. PATENT DOCUMENTS

| 5,776,701 A * | 7/1998 | Mans et al. .............. 435/7.4 |
| 6,214,980 B1 | 4/2001 | Peck et al. |
| 6,485,982 B1 * | 11/2002 | Charlton ............... 436/514 |
| 6,506,575 B1 | 1/2003 | Knappe et al. |
| 6,929,940 B1 | 8/2005 | Richards et al. |

OTHER PUBLICATIONS

Hong et al. "Rapid and convenient determination of oxalic acid employing a novel oxalate biosensor based on oxalate oxidase and SIRE technology" Biosensors and Bioelectronics 18 (2003) 1173-1181.*
Yriberri et al. "A Semi-Automatic Enzymic Method for Estimating Urinary Oxalate" 1980 Clin. Chem 26(7) 881-884.*
Costello et al "An enzymic method for the spectrophometric determination of oxalic acid" 1976 J Lab Clin Med 87(5) 903-908.*
Manchenko Handbook of detection of enzymes on electrophoretic gels 2003 CRC Press.*
Libios Oxalate Assay Kit Jan. 2006.*
International Preliminary Report on Patentability—PCT/US2012/024164, Sep. 26, 2012.
International Search Report of PCT/US2012/024164, Sep. 26, 2012.
Hong, F. et al., Rapid and convenient determination of oxalic acid employing a novel oxalate biosensor based on oxalate oxidase and SIRE technology; Biosens, Bioelectron., Aug. 15, 2003, vol. 18, No. 9, pp. 1173-1181.
Godara, S., et al.; Urinary & serum oxalate determination by oxalate oxidase immobilized on to affixed arylamine glass beads; Indian J. Med. Res., Apr. 2008, vol. 127, No. 4, pp. 370-376.

* cited by examiner

*Primary Examiner* — Suzanne M Noakes
*Assistant Examiner* — Gerard Lacourciere
(74) *Attorney, Agent, or Firm* — Locke Lord LLP; Jeffrey D. Hsi (57) ABSTRACT

The present invention features compositions and methods for the detection or measurement of oxalate in a sample. Such compositions include test devices that provide for the rapid and accurate detection of oxalate in a sample from a biological fluid. Advantageously, the compositions can be used to monitor the oxalate levels of a patient at a point of care (e.g., at the patient's home, clinic, physician's office, or other clinical setting).

24 Claims, 6 Drawing Sheets

COMPOSITIONS AND METHODS FOR MONITORING OXALATE

CROSS-REFERENCE TO RELATED APPLICATION

This application is the U.S. national stage application of PCT International Application No. PCT/US2012/024164, filed Feb. 7, 2012, which claims the benefit of the following U.S. Provisional Application No. 61/440,133, filed Feb. 7, 2011, the entire contents of which are incorporated herein by reference.

BACKGROUND OF THE INVENTION

Kidney stones are a common disorder of the urinary tract, which are caused by a buildup of minerals in urine. While many stones pass painlessly through the urinary system, larger stones may cause debilitating pain and may have to be surgically removed. About 1 million Americans get kidney stones per year. Some of these individuals have a family history of kidney stones. The most common type of kidney stones is formed from calcium oxalate. Patients prone to kidney stone formation are typically placed on a low oxalate diet. However, patient compliance with dietary restrictions is problematic. Methods for monitoring oxalate levels in biological samples of a patient throughout the day would allow the patient to increase water consumption or reduce oxalate consumption to prevent stone formation. Such methods would also enhance patient compliance with dietary restrictions by providing almost immediate feedback on the impact of diet on oxalate levels.

SUMMARY OF THE INVENTION

As described below, the present invention features compositions and methods suitable for monitoring oxalate levels in a biological sample (e.g., fresh urine sample). Such methods are amenable to use in a patient's home, physician's office, or at any other site where patient care is carried out. Test devices of the invention provide for the rapid and accurate detection of oxalate levels in a biological fluid (e.g., urine, blood, plasma).

In one aspect, the invention provides a test device for detecting oxalate in a liquid sample, the device comprising oxalate oxidase, and an indicator system that provides a detectable reaction product in response to hydrogen peroxide production. In particular embodiments, the indicator system comprises 3-methyl-2-benzothiazolinone hydrazone (MBTH) and 3-(dimethylamino) benzoic acid (DMAB).

In one aspect, the invention provides a test device for detecting oxalate in a liquid sample, the device comprising oxalate decarboxylase, and an indicator system that provides a detectable reaction product in response to formate production. In particular embodiments, the indicator system comprises phenazine methosulfate (PMS) and iononitro tetrazolium (INT).

In one aspect, the invention provides a test device for detecting oxalate in a liquid sample, the device including a liquid permeable material defining the following portions in capillary communication: a site for application of a liquid sample, including a liquid permeable medium; a second portion including a liquid permeable medium; and a third portion that is the site for detecting the presence of oxalate at the test site, the third portion including a liquid permeable medium having an enzyme system having oxalate specific enzyme activity fixed to the medium at the test site, the enzyme system including oxalate specific enzyme, a substance which reacts with a reaction product of the oxalate specific enzyme, and an indicator material which reacts in the presence of the reaction product and changes color.

In a related aspect, the invention provides a method for detecting an analyte in a liquid sample, the method involving: applying a liquid sample to a test device according to an aspect of the invention; and detecting presence or absence of oxalate at a test site, where the presence of color change at the test site identifies the presence of oxalate in the sample and the absence of color change at the test site identifies the absence of the oxalate in the sample.

In another related aspect, the invention provides a method for detecting oxalate in a liquid sample, the method comprising: applying a liquid sample to a test device according to an aspect of the invention; providing for the flow of the liquid from the site of application to the test site; and detecting presence or absence of oxalate at a test site, where the presence of color change at the test site identifies the presence of oxalate in the sample and the absence of color change at the test site identifies the absence of the oxalate in the sample.

In another aspect, the invention provides a kit containing a reaction mix, the reaction mix including an enzyme system having oxalate specific enzyme activity, the enzyme system including oxalate specific enzyme, a substance which reacts with a reaction product of the oxalate specific enzyme, and an indicator which reacts in the presence of the reaction product and changes color; and a color chart.

In a related aspect, the invention provides a kit comprising a test device according to an aspect of the invention.

In still another related aspect, the invention provides an instrument for determining oxalate concentrations in a sample, said instrument including: a port to receive a test device according to an aspect of the invention that includes a component for detecting color change; a light source; a detector for detecting reflectance from the support; and a display for displaying a result of oxalate presence.

In various embodiments of any of the aspects delineated herein, the enzyme system has oxalate oxidase activity, the enzyme system including oxalate oxidase, a substance having peroxidative activity, an indicator material which is oxidized in the presence of peroxide, and a substance having peroxidative activity and changes color. In various embodiments of any of the aspects delineated herein, the enzyme system has oxalate decarboxylase activity, the enzyme system including an oxalate decarboxylase, a substance having formate dehydrogenase activity, and an indicator material which is reduced in the presence of formate and changes color.

In various embodiments of any of the aspects delineated herein, the test device includes a liquid permeable substrate. In specific embodiments, the liquid permeable substrate is in the form of a strip. In various embodiments of any of the aspects delineated herein, the device includes oxalate oxidase or oxalate decarboxylase and the indicator system in powder form, and the device is suitable for containing a liquid. In specific embodiments, the test device is in the form of a clear liquid container (e.g., cuvette).

In various embodiments of any of the aspects delineated herein, the second portion includes an agent that alters the composition of the liquid as it contacts the second portion. In various embodiments of any of the aspects delineated herein, the second portion comprises a liquid permeable material that acts as a filter to remove particulates. In various embodiments of any of the aspects delineated herein, the second portion comprises an agent (e.g., a buffer, a surfactant, or a salt) that alters a physical characteristic (e.g., pH, salt concentration, or buffering capacity of the liquid sample) of a liquid sample flowing through the second portion.

In various embodiments of any of the aspects delineated herein, the test device further includes a fourth portion that acts as a wick, the fourth portion including sorbent material. In various embodiments of any of the aspects delineated herein, the fourth portion including absorbent material that facilitates the flow of liquid through the device.

In various embodiments of any of the aspects delineated herein, the test device or kit is used at a point of care. In various embodiments of any of the aspects delineated herein, the liquid sample is blood, urine, or saliva. In various embodiments of any of the aspects delineated herein, the test device further includes a solid support selected from the group consisting of a sheet, tube, and stick. In various embodiments of any of the aspects delineated herein, the color change is detected by visual inspection. In various embodiments, the color change is compared to a standard for detecting a difference in color of said sample In various embodiments of any of the aspects delineated herein, the kit includes one or more of a powdered reaction mix, a reconstitution buffer, and dispensing pipette. In various embodiments of any of the aspects delineated herein, the kit includes a standard for detecting a difference in color of said sample In various embodiments of any of the aspects delineated herein, the kit includes instructions for the use of the kit or device for the detection of oxalate.

The invention provides compositions and methods suitable for monitoring oxalate levels at a point of care (e.g., at a patients' home, clinic, physician's office, or other clinical setting). Advantageously, methods of the invention do not require sophisticated laboratory equipment, but can be carried out by a patient at home, in a physician's office, or at other sites where patient care is carried out. Compositions and articles defined by the invention were isolated or otherwise manufactured in connection with the examples provided below. Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any biological or synthetic chemical compound. Exemplary agents include salts, detergents, buffers, acids, bases, polypeptides, nucleic acid molecules, or fragments thereof.

By "alteration" is meant a change (increase or decrease) in the levels or activity of an analyte, gene or polypeptide as detected by standard art known methods such as those described herein. As used herein, an alteration includes a detectable change in the level of oxalate. Such a change may be by about 10%, 25%, 50%, 75% or more. Levels of oxalate may be monitored by detecting, for example, formate or peroxide levels, using a visual readout.

By "alters the composition of the liquid" is meant produces a change in a physical property of the liquid.

By "ameliorate" is meant decrease, suppress, attenuate, diminish, arrest, or stabilize the development or progression of a disease.

By "analyte" is meant any compound under investigation using an analytical method. In various aspects of the invention, levels of the analyte oxalate are monitored.

By "analyte-binding conjugate" is meant a detectable molecule that binds a compound under investigation.

By "biological sample" is meant any tissue, cell, fluid, or other material derived from an organism (e.g., human subject). In various embodiments, biological samples include, for example, urine, blood, plasma, feces, gastric samples, mucous, and semen. In various embodiments, biological fluids include, for example, urine, blood, plasma, gastric samples, mucous, saliva, and semen.

By "capillary communication" is meant facilitating the flow of a liquid between liquid permeable materials.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "decarboxylase activity" is meant the activity of an enzyme that catalyzes the addition or removal of a carboxyl group from a compound (e.g., oxalate). An enzyme having decarboxylase activity used in the invention is oxalate decarboxylase.

By "dehydrogenase activity" is meant an activity of an enzyme that oxidizes a substrate by a reduction reaction that transfers one or more hydrides ($H^-$) to an electron acceptor (e.g., $NAD^+/NADP^+$ to NADH/NADPH). An enzyme having dehydrogenase activity used in the invention is formate dehydrogenase.

"Detect" refers to identifying the presence, absence or amount of the analyte to be detected.

By "indicator system" is meant a system that produces a colored or detectable derivative of a labeled molecule when incubated with a proper substrate, allowing it to be detected and/or quantified. Indicator systems may further comprise one or more enzymes. In particular embodiments of the invention, the indicator system comprises 3-methyl-2-benzothiazolinone hydrazone (MBTH), 3-(dimethylamino) benzoic acid (DMAB), and peroxidase for the detection of hydrogen peroxide (e.g., produced by oxalate oxidase). In other embodiments of the invention, the indicator system comprises phenazine methosulfate (PMS), iononitro tetrazolium (INT), NAD, and formate dehydrogenase for the detection of formate (e.g., produced by oxalate decarboxylase).

By "lateral flow device" is meant a test device that relies on the flow of a liquid via capillary action, wicking, or wetting a liquid permeable media present in the device.

By "liquid permeable material" is meant a material susceptible to wetting, wicking, or transport of a liquid by capillary action.

By "marker" is meant a marker having an alteration in level that is associated with a disease or disorder.

By "oxidase activity" is meant the activity of an enzyme that catalyzes an oxidation-reduction reaction involving molecular oxygen ($O_2$) as the electron acceptor (e.g., reducing oxygen is reduced to hydrogen peroxide ($H_2O_2$)). An enzyme having oxidase activity used in the invention is oxalate oxidase.

By "peroxidative activity" is meant the activity of an enzyme that catalyzes a reaction of the form: ROOR'+electron donor (2 e–)+2H+→ROH+R'OH. An enzyme having peroxidative activity used in the invention is horseradish peroxidase.

By "portion" is meant some fraction of a whole. A portion of a test device, for example, may be 0.1, 0.2, 0.3, 0.4, 0.5, 0.6, 0.7, 0.8, 0.9 of the length of the interior flow path of the device.

By "product" or "reaction product" is meant a compound produced by the reaction of one or more compounds reaction, e.g., in the presence of an enzyme. For example, hydrogen peroxide and carbon dioxide are reaction products of the reaction of oxalate and oxygen in the presence of oxalate oxidase.

By "reduces" is meant a negative alteration of at least 10%, 25%, 50%, 75%, or 100%.

By "reference" is meant a standard or control condition.

By "sample application site" is meant the portion of the device that contacts a liquid under analysis.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "test device" is meant a device used in the detection of an analyte in a sample.

By "wick" is meant sorb (e.g., absorb, adsorb) a liquid.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 3A-3C depict assays to test for oxalate using test device strips imbedded with oxalate oxidase enzyme.

FIGS. 4A-4G show the enzyme activity of specific quantities of the oxalate oxidase enzyme in a constant amount of oxalate, thus representing a dilution curve of the enzyme.

DETAILED DESCRIPTION OF THE INVENTION

The invention features compositions and methods that are useful for monitoring oxalate levels in a biological sample of a subject. Current methods for monitoring oxalate levels are performed in diagnostic laboratories and require twenty-four hour urine collections. Advantageously, the present invention provides for the monitoring of oxalate levels in fresh urine or blood samples at a point of care (e.g., patient's home, physician's office).

Oxalate Detection

Oxalate was confirmed as a normal constituent of urine in 1951, but only recently has the significance of calcium oxalate crystalluria and its relationship to urinary tract stone formation been fully recognized. Formation of the sparingly soluble calcium salt of oxalate in the urinary tract is considered a major factor in urolithiasis. In the urine, oxalate is a very strong promoter of calcium oxalate precipitation.

Oxalate present in a biological sample can be easily detected by oxidizing oxalate to form hydrogen peroxide. Hydrogen peroxide is then detected as a readout of oxalate levels using any method known in the art.

Enzymes for converting oxalate to hydrogen peroxide include oxalate oxidase. Optimum oxalate oxidase concentration depends on the composition of the indicator system. Oxalate oxidase activity in the range from about 500-10,000 U/mL is generally suitable, preferably from about 700-2000 U/mL. Generally, higher concentrations of oxalate oxidase cause the reaction to proceed more rapidly and lower concentrations, less rapidly. Optimum concentration can be determined by routine experimentation.

In one exemplary reaction, oxalate oxidase catalyzes the oxidation of oxalate to carbon dioxide and peroxide ($H_2O_2$). The hydrogen peroxide reacts with 3-methyl-2-benzothiazolinone hydrazone (MBTH) and 3-(dimethylamino) benzoic acid (DMAB) in the presence of peroxidase to yield an indamine dye, which has an absorbance maximum of 590 nm. The intensity of the color produced is directly proportional to the concentration of oxalate in the sample.

Principle $$\text{Oxalate} + O_2 \xrightarrow{\text{Oxalate Oxidise}} 2CO_2 + H_2O_2$$

$$H_2O_2 + \text{MBTH} + \text{DMAB} \xrightarrow{\text{Peroxidase}} \text{Indamine Dye } H_2O$$

In a specific embodiment, the hydrogen peroxide so produced reacts with the component for detecting hydrogen peroxide, which comprises, for example, a peroxidase that selectively catalyzes a reaction between the hydrogen peroxide and an indicator. The peroxidase uses hydrogen peroxide as an oxidant which is capable of removing hydrogen atoms from various substrates. A suitable peroxidase may contain ferriprotoporphyrin, a red hemin obtained from plants. Peroxidases obtained from animals, for example from the thyroid glands of animals, are also suitable. Horseradish peroxidase (HRPO) is one example of a constituent of the component for detecting hydrogen peroxide. Chromogenic substrates of peroxidase include, without limitation, N,N-Dimethyl-1,4-phenylene-diamine Dihydrochloride, 1-Naphthol, 3-Amino-9-ethylcarbazole, 4-Chloro-1-naphthol, 3,3'-Diaminobenzidine, 3,3'-Diaminobenzidine Tetrahydrochloride Hydrate, o-Dianisidine Dihydrochloride, o-Dianisidine, 4-Aminoantipyrine Hydrochloride, 4-Aminoantipyrine, 5-Aminosalicylic Acid, 2,4-Dichlorophenol, N,N-Dimethylaniline N,N-Diethyl-m-toluidine, 2,4,6-Tribromo-3-hydroxybenzoic Acid, 2,2'-Azinobis(3-ethylbenzothiazoline-6-sulfonic Acid Ammonium Salt), 1,2-Phenylenediamine, and 3,3',5,5'-Tetramethylbenzidine. The hydrogen peroxide, preferably catalyzed by a peroxidase, reacts either directly or indirectly with a substrate to form an indicator dye. The indicator dye may reduce reflectance at the testing surface. Testing surface reflectance is typically measured at two wavelengths (e.g., about 590 nm and about 700 nm).

The following patents are cited and incorporated by reference for general background of devices that utilize reflectance produced from breakdown of an analyte and production of hydrogen peroxide. U.S. Pat. No. 4,935,346, issued Jun. 19, 1990 to R. Phillips et al., discloses a meter, strip, and method for determining the glucose concentration in a sample of whole blood (see also U.S. Pat. No. 5,304,468). The method involves simply applying a sample of whole blood to a first ("sample") surface of an inert porous matrix that is impregnated with a reagent. The sample migrates toward the opposite, "testing" surface, as the analyte glucose interacts with the reagent to produce a light-absorbing reaction product. A reading of reflectance from the testing surface indicates the glucose concentration. Reflectance measurements are made at two separate wavelengths in order to eliminate interferences. A timing circuit is triggered by an initial decrease in reflectance caused by wetting of the testing surface by the sample having passed through the matrix. U.S. Pat. No. 5,306,623, issued Apr. 26, 1994 to Kiser et al., discloses a visual blood glucose test strip that involves applying a glucose-containing whole blood sample to one side of the strip and taking the glucose reading on the opposite side, after red blood cells have been separated out and the sample has reacted with a reagent in the strip. An anisotropic polysulfone membrane was found especially useful as a single layer matrix for the strip. U.S. Pat. No. 5,453,360, issued Sep. 26, 1995 to Y. S. Yu, discloses a dye couple useful in dry reagent strips for detecting analytes in biological fluids. The dye couple comprises 3-methyl-2-benzothiazolinone hydrazone and 8-anilino-1-naphthalenesulfonate and is used as an indicator in a reaction cascade producing a strong oxidizing agent, such as hydrogen peroxide. An advantage of the couple is that it is soluble in aqueous solution, but becomes insoluble upon oxidative coupling, thereby minimizing fading and providing a stable endpoint.

A meter that has come into widespread use for self-monitoring of blood glucose is the One Touch® II meter, which uses a strip that is described in U.S. Pat. Nos. 4,935,346 and 5,304,468, discussed above. The meter and strip permit a user to measure glucose concentration in a whole blood sample quickly, easily, and accurately. The sample is applied to one surface of the strip and the measurement made on the opposite surface. A portion of the whole blood sample penetrates from the sample surface to the testing surface, and the blood color can be observed from the testing surface. Certain embodiments of the present invention can be adapted for use with traditional glucose meters such as one working on principles similar to the One Touch® meter. In a specific embodiment, the invention pertains to a system for detecting oxalate that comprises a strip or similar substrate having oxalate oxidase embedded thereon. The strip is contacted with a biological sample such as blood or urine and any oxalate in the specimen reacts with the oxalate oxidase on the strip to produce hydrogen peroxide. The strip also has embedded thereon a component for detecting hydrogen peroxide. When hydrogen peroxide is produced the component for detecting hydrogen peroxide causes a reflectance change that can be detected by a suitable instrument.

Oxalate decarboxylase is a manganese dependent enzyme that catalyzes the conversion of oxalate to formate and carbon dioxide. In another exemplary reaction, oxalate decarboxylase catalyzes the decarboxylation of oxalate to formate and $CO_2$. Formate dehydrogenase is then oxidized to $CO_2$ in the presence of β-nicotinamide adenine dinucleotide.

$$\text{Oxalate} \xrightarrow{\text{Oxalate decarboxylase}} \text{Formate}$$

$$\text{Formate} + \text{NAD} \xrightarrow{\text{Formate dehydrogenase}} CO_2 + \text{NADH}$$

$$\text{NADH} + \text{PMS} \longrightarrow \text{NAD} + \text{PMS—H}$$

$$\text{PMS—H} + \text{INT} \longrightarrow \text{PMS} + \text{reduced-INT (blue color)}$$

[PMS = phenazine methosulfate; INT = iononitro tetrazolium]

The formate can then be detected using a variety of techniques known in the art. In a preferred embodiment, the production of formate is measured colorimetrically by linking the catabolism of formate with the production of a detectable color change (e.g., the formation of a compound that absorbs a particular wavelength of light). For example, formate in the presence of the co-factor NAD and the enzyme formate dehydrogenase reduces NAD to NADH. NADH in the presence of phenazine methosulfate (PMS) forms an intermediate that in the presence of a tetrazolium salt (e.g., iononitrotetrazolium (INT) or other tetrazolium compounds) produces a color change of the dye. The use of iononitrotetrazolium (INT) causes a solution containing oxalate to turn blue. The production of formate is directly correlated with the amount of oxalate present in the sample. Therefore, if a known amount of formate is produced using the subject enzyme system, then the amount of oxalate present in the sample can be easily quantitated. The assay systems described herein may also be used to identify or screen for oxalate oxidase and oxalate decarboxylase activity in a sample.

Diagnostics

The present invention provides methods of treating disease and/or disorders or symptoms thereof which comprise administering a therapeutically effective amount of a pharmaceutical composition comprising a compound of the formulae herein to a subject (e.g., a mammal such as a human). In one embodiment, the invention provides a means of identifying a patient in need of treatment and/or monitoring treatment progress. The method includes the step of determining a level of diagnostic marker (Marker, e.g., oxalate). Thus, one embodiment is a method of treating a subject suffering from or susceptible to an oxalate related disease or disorder or symptom thereof (e.g., kidney stone formation, vulvodynia, hyperoxaluria type 1, autism, intestinal resections, among others). The method includes the step of administering to the mammal a therapeutic amount of an amount of a compound herein sufficient to treat the disease or disorder or symptom thereof, under conditions such that the disease or disorder is treated. For elevated oxalate urine levels, one treatment is to increase water or fluid intake to increase voided volumes.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with elevated oxalate levels, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Design of a Test Device

The test device can take any form desired that provides for the flow of a liquid test sample from the point of contact with the test sample past the test and/or control sites. In general, the test device of the present invention includes an interior flow pathway that includes one or more liquid permeable materials. In one example, the solid substrate is a hydrophilic porous matrix to which reagents may be covalently or non-covalently bound. The matrix allows for the flow of an aqueous medium through it. It also allows for binding of protein compositions to the matrix without significantly adversely affecting the biological activity of the protein, e.g. enzymatic activity of an enzyme. To the extent that proteins are to be covalently bound, the matrix will have active sites for covalent bonding or may be activated by means known to the art. The composition of the matrix is reflective, and it has sufficient thickness to permit the formation of a light absorbing dye in the void volume or on the surface to substantially affect the reflectance from the matrix. The matrix may be of a uniform composition or a coating on a substrate providing the necessary structure and physical properties, such as hydrophilicity. Polysulfones and polyamides (nylons) are examples of suitable matrix materials. Other polymers having comparable properties may also be used. The polymers may be modified to introduce other functional groups which provide for charged structures, so that the surfaces of the matrix may be neutral, positive, or negative.

In a first portion, the device includes a site for the application of a liquid sample.

The second portion of the device has a variety of features that enhance functionality. In one embodiment, the second portion is composed of a material capable of filtering the sample to prevent the flow of particulate matter through the device. In another embodiment, the second portion facilitates complex formation by increasing the time required for the liquid to flow from the site of application to the test site. Accordingly, the dimensions of the second portion may be altered (e.g., increased or decreased) to empirically determine for each application those dimensions that enhance sensitivity while reducing false positives, i.e., optimizing the signal-to-noise ratio. In yet another embodiment, the second portion of the device can be used to deliver a desired agent to the liquid as it flows through the device. For example, the second portion may be impregnated with a buffer (e.g., TRIS, sodium carbonate), surfactant (e.g., Tween, Triton), preservative (e.g., Na azide, thimerosol), salt, or other agent, such that contact of the sample with the second portion of the device alters the sample. Exemplary alterations include an increase or decrease in the pH of the sample, in the salt concentration, in the buffering capacity, or in the binding between the conjugate and the analyte.

The third portion of the device includes a test site, which acts as a readout zone that provides for detection of oxalate in the sample. Various means for detecting the presence of an analyte at a test site are known in the art. In various embodiments, an enzyme system having oxalate specific enzyme activity is fixed to the medium at the test site, the enzyme system comprising an oxalate specific enzyme, a substance which reacts with a metabolite of the oxalate specific enzyme, and an indicator material which reacts in the presence of the metabolite and changes color. Oxalate specific enzyme activity in the range from about 500-10,000 U/mL is generally suitable, preferably from about 700-2000 U/mL. Optimum oxalate specific enzyme concentration depends on the composition of the indicator system, and can be determined by routine experimentation. In some embodiments, the oxalate specific enzyme is oxalate oxidase (e.g., a purified and/or recombinant oxalate oxidase). In other embodiments, the oxalate specific enzyme is oxalate decarboxylase (e.g., a purified and/or recombinant oxalate decarboxylase). In this approach, detection of color or a color change indicates the presence of oxalate in the sample.

It may be desirable to include a positive control to indicate that the liquid sample has traversed the interior flow path from the site of application past the test site.

The device may also include in a fourth portion a wicking pad that contains sorbent material capable of absorbing or adsorbing excess liquid present in the liquid sample.

In one embodiment, the test device contains a liquid permeable material defining the following portions in capillary communication:

a) a first portion that is the site for application of a liquid sample, comprising a liquid permeable medium, where the first portion is between 5 mm and 20 mm in length; for example, the length of the first portion is equal to any integer between 5 and 20 (5, 10, 15, 20 mm in length);

b) a second portion comprising a liquid permeable medium, where the second portion overlaps the first portion by at least 1, 2, 3, 4, or 5 mm; and the length of the second portion is between 10 mm and 40 mm; for example, the length of the second portion is any integer between 10 and 40 (e.g., 10, 15, 20, 25, 30, 35, 40); and c) a third portion that is the site for detecting the presence of oxalate at the test site, the third portion comprising a liquid permeable medium having an enzyme system having oxalate specific enzyme activity fixed to the medium at the test site, the enzyme system comprising oxalate specific enzyme, a substance which reacts with a metabolite of the oxalate specific enzyme, and an indicator material which reacts in the presence of the metabolite and changes color, wherein the third portion is between 15 and 40 mm in length; for example, is any integer between 15 and 40 (e.g., 15, 20, 25, 30, 35, 40); and the second portion overlaps the third portion by at least 1, 2, 3, 4, or 5 mm.

In a fourth portion the device contains sorbent material. The sorbent material has a length between 25 and 75 mm. For example, the length is an integer between 25 and 75 (e.g., 25, 35, 50, 60, 70, 75). In one embodiment, the fourth portion overlaps the third portion by at least 1, 2, 3, 4, or 5 mm.

Figure 1:
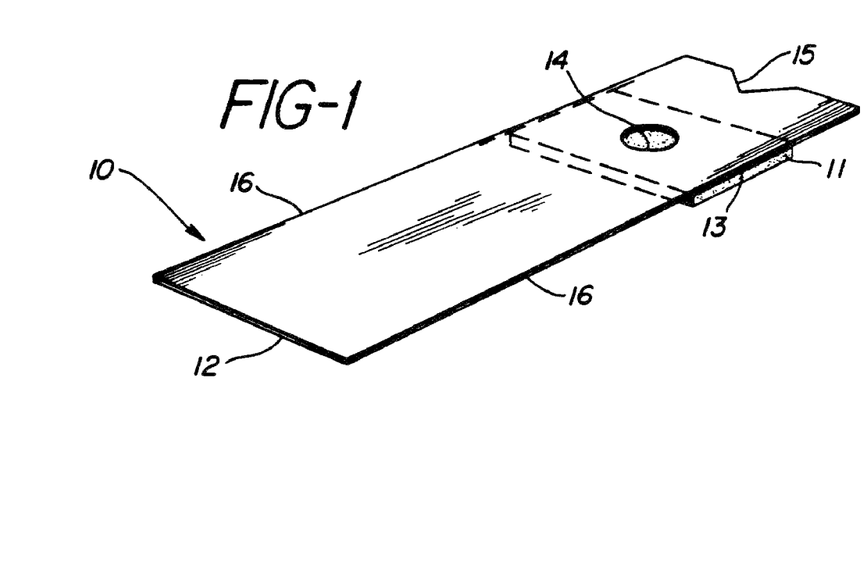
FIG. 1 shows an embodiment of a strip that includes reagent pad 11 so that a sample can be applied to one side of the reagent pad 11 while light reflectance is measured from the side of the reagent pad 11 opposite the location where sample is applied.

In general the interior flow path is between 1 mm and 10 mm in width; for example, the width of a test device (e.g., test strip) is any integer between 1 and 10 (e.g., 1, 2, 3, 4, 5, 6, 7, 8, 9, 10). In one embodiment the width of the strip is 3.8 mm. The design and dimensions of an exemplary test strip of the invention are shown in FIG. 1. Desirably, a test device of the invention has increased sensitivity relative to a conventional test device. Sensitivity of a test device of the invention is increased by at least 5%, 10%, 25%, 50%, 75%, 100%, 150%, or 200% relative to a conventional test device.

A schematic diagram showing an exemplary test device is provided at FIG. 1, which shows an embodiment of a strip that includes reagent pad 11 so that a sample can be applied to one side of the reagent pad 11 while light reflectance is measured from the side of the reagent pad 11 opposite the location where sample is applied.

Figure 2:
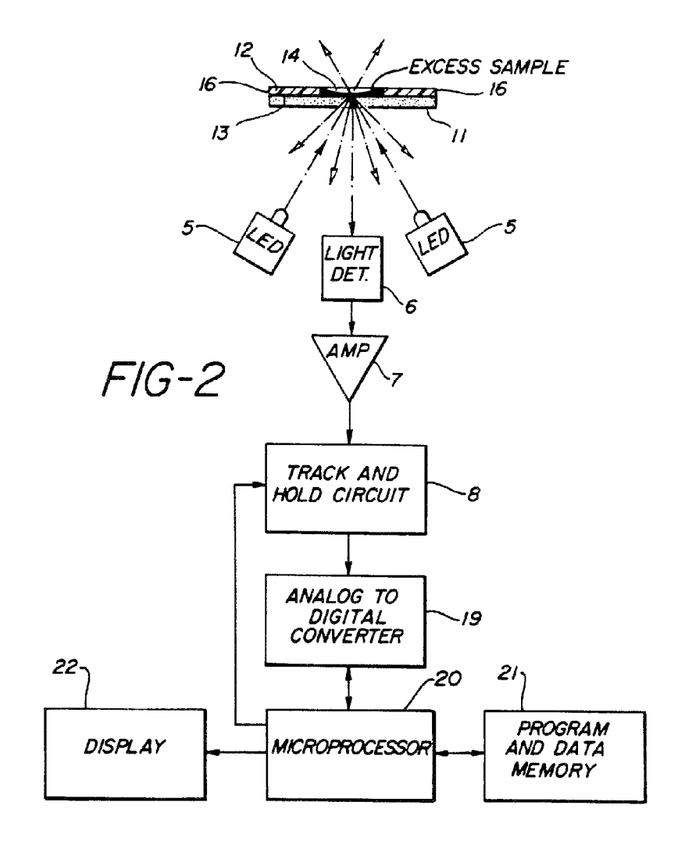
FIG. 2 shows a system in which the reagent is applied to the side with the hole 14 in the backing handle 12 while light is reflected and measured on the other side of the reagent pad 11.

FIG. 2 shows a system in which the reagent is applied to the side with the hole 14 in the backing handle 12 while light is reflected and measured on the other side of the reagent pad 11. Other structures than the one depicted may be employed. The pad 11 may take various shapes and forms, subject to the limitations provided herein. The pad 11 will be accessible on at least one surface and usually two surfaces. A reagent element may be attached to the support by any convenient means, e.g., a holder, clamp or adhesives; however, in the illustrated embodiment it is bonded to the backing. Methods of bonding include, but are not limited to, use of any non-reactive adhesive, by a thermal method in which the backing surface is melted enough to entrap some of the material used for the reagent element, or by microwave or ultrasonic bonding methods which likewise fuse the hydrophilic sample pads to the backing. It is important that the bonding the such as to not itself interfere substantially with the diffuse reflectance measurements or the reaction being measured, although this is unlikely to occur as no adhesive need be present at the location where the reading is taken. For example, an adhesive 13 can be applied to the backing strip 12 followed first by punching hole 14 into the combined strip and adhesive and then applying reagent pad 11 to the adhesive in the vicinity of hole 14 so that the peripheral portion of the reagent pad attaches to the backing strip.

Interior Flow Path

The test device comprises an interior flow path that facilitates the flow of a liquid sample through the device. This interior flow path contains one or more liquid permeable materials or membranes composed of any relatively inert material or a combination of materials suitable for transporting a liquid (e.g., glass fibers, polyester, nitrocellulose, fibers of cellulose or derivatives thereof, non-cellulose hydrocarbon materials, ceramics) from the contact site past the test and/or control sites and, optionally, into a reservoir. Suitable materials for use in the interior flow path are wettable and exhibit low non-specific binding. Materials having increased sorptivity promote the flow of liquid. Different materials having different absorption characteristics or sorptivities may be used in various portions of the flow path. If desired, the materials to be used are screened for optimal pore size and density in order to facilitate the controlled distribution of an antibody within a membrane, to optimize reaction kinetics, or to optimize the sensitivity, discriminatory ability, or signal-to-noise ratio of the device.

Solid Supports

For most applications, the test device includes an interior flow pathway fixed to a solid support. The physical shape of the solid support is not critical, although some shapes may be more convenient than others for the present purpose. Accordingly, the solid support may be in the shape of a paper strip, dipstick, membrane (e.g. a nylon membrane or a cellulose filter), a plate (e.g. a microtiter plate) or solid particles (e.g. latex beads). The solid support may be made of any suitable material, including but not limited to a plastic (e.g., polyethylene, polypropylene, polystyrene, latex, polyvinylchloride, polyurethane, polyacrylamide, polyvinylalcohol, nylon, polyvinyl acetate, or any suitable copolymers thereof), cellulose (e.g. various types of paper, such as nitrocellulose paper and the like), a silicon polymer (e.g. siloxane), a polysaccharide (e.g. agarose or dextran), or an ion exchange resin (e.g. conventional anion or cation exchange resins).

Sorbent Reservoir

The test device optionally includes a fourth portion that forms a reservoir of adsorbent or absorbent material. This reservoir sorbs excess liquid as it flows through the test device. For some applications, such as where the concentration of oxalate is particularly low, it may be desirable to apply large volumes of a liquid test sample to the test device. In such cases, the presence of the adsorbent material may enhance the sensitivity of oxalate detection. Optionally, the region of the flow path in the test cell defining the test and control sites is restricted in cross-sectional area relative to other regions of the flow path. This feature produces a "bottle-neck" effect wherein the oxalate in the entire volume of adsorbed sample must pass through an area of restricted flow immediately above the test site. This "bottle-neck" may facilitate sandwich formation. Suitable sorbent materials include virtually any commercial material (e.g., synthetic or natural materials, such as cotton) capable of absorbing many times its weight in water. Such materials are widely available in commerce.

Capture Molecule

The test device optionally includes a portion that contains a capture molecule. In a specific embodiment, the oxalate capture molecule is a calcium binding protein. Depending on the sample and level of capture desired, the calcium binding proteins, or other oxalate capture molecules used, may be pretreated with calcium thereby resulting in loaded calcium proteins. In a further embodiment, the calcium binding proteins are attached to the substrate. In a more specific embodiment, the calcium binding proteins are attached to the substrate by linker molecules. In an alternative embodiment, the calcium binding proteins are embedded in the substrate. In a further embodiment, the invention pertains to a micro-particle linked to an oxalate capture molecule (e.g., calcium ions which bind oxalate in the biological sample). The particle is associated with a thiol group which is bound to a linker molecule such as PEG. Those skilled in the art will appreciate that other linker molecules known in the art could be used in accordance with the teachings herein. The linker is associated with an oxalate capture molecule. The microparticles can be applied to a solid substrate. In a preferred embodiment, the microparticles are printed onto a substrate.

Methods of Using the Test Device

The invention provides methods of using a test device of the invention for the detection of oxalate in a test sample. In one example, the assay is conducted by placing the leading edge (first portion) of a lateral flow device in contact with a liquid test sample. In another example, the sample is brought into contact with the device by applying a liquid test sample to the first portion of the lateral flow device in a drop-wise fashion.

Test Samples

Methods and compositions of the invention are useful for the identification of oxalate in a test sample. In one embodiment, the methods of the invention are suitable for detecting analytes of biological origin. Test samples include, but are not limited to, any liquid containing a dissolved or dispersed analyte of biological origin. Exemplary test samples include body fluids (e.g. blood, serum, plasma, amniotic fluid, sputum, urine, cerebrospinal fluid, lymph, tear fluid, feces, or gastric fluid), or feces. If the test sample is not in itself sufficiently fluid for the present purpose, it may be admixed with a suitable fluid to the desired fluidity.

Kits

The invention provides kits that include a composition or a test device for the detection of oxalate in a sample. In one embodiment, the kit includes a powdered reaction mix and a reconstituting reaction buffer described herein. In some embodiments, the kit comprises a container, which contains the powdered reaction mix and another container, which contains reconstituting reaction buffer; such containers can be boxes, ampoules, bottles, vials, tubes, bags, pouches, blister packs, or other suitable container forms known in the art. In one embodiment, such containers may be sterile. Such containers can be made of plastic, glass, laminated paper, metal foil, or other materials suitable for holding medicaments. The powder formulation may include an oxalate specific enzyme composition to catalyze and detect oxalate in the biological sample after exposing said substrate to a biological sample containing oxalate, and a chromogenic reactive substrate for detecting whether the sample contains oxalate. This method provides for rapid, inexpensive, easy to use testing for oxalate in a sample. A color change may be detected as a difference in the hue or shade of color. The change in color may be indicative of either the presence or the quantity of oxalate in a sample. In one embodiment, a color chart for visually scoring the presence of oxalate in the sample is included.

In one embodiment, the kit includes a lateral flow device described herein. In some embodiments, the kit comprises a container, which contains the lateral flow device; such containers can be boxes, ampoules, bottles, vials, tubes, bags, pouches, blister packs, or other suitable container forms known in the art. In one embodiment, such containers may be sterile. Such containers can be made of plastic, glass, laminated paper, metal foil, or other materials suitable for holding medicaments.

If desired, the composition or device is provided together with instructions for using it to identify the presence or absence of oxalate in a sample. The instructions will generally include information about the use of the device for the identification of a particular analyte, such as oxalate in a liquid sample (e.g., an environmental sample, biological sample, or liquid sample extracted from an agricultural commodity). The instructions may be printed directly on the container (when present), or as a label applied to the container, or as a separate sheet, pamphlet, card, or folder supplied in or with the container. If desired, the kit may also include a color chart. The color chart provides a means of indicating the oxalate levels in the sample base on the color reaction. If desired, the kit may also include a standard measure pipet, a test vial, and/or a liquid (e.g., suitable buffer, such as phosphate buffered saline, or water) to be used in the extraction of a sample.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Figure 3:
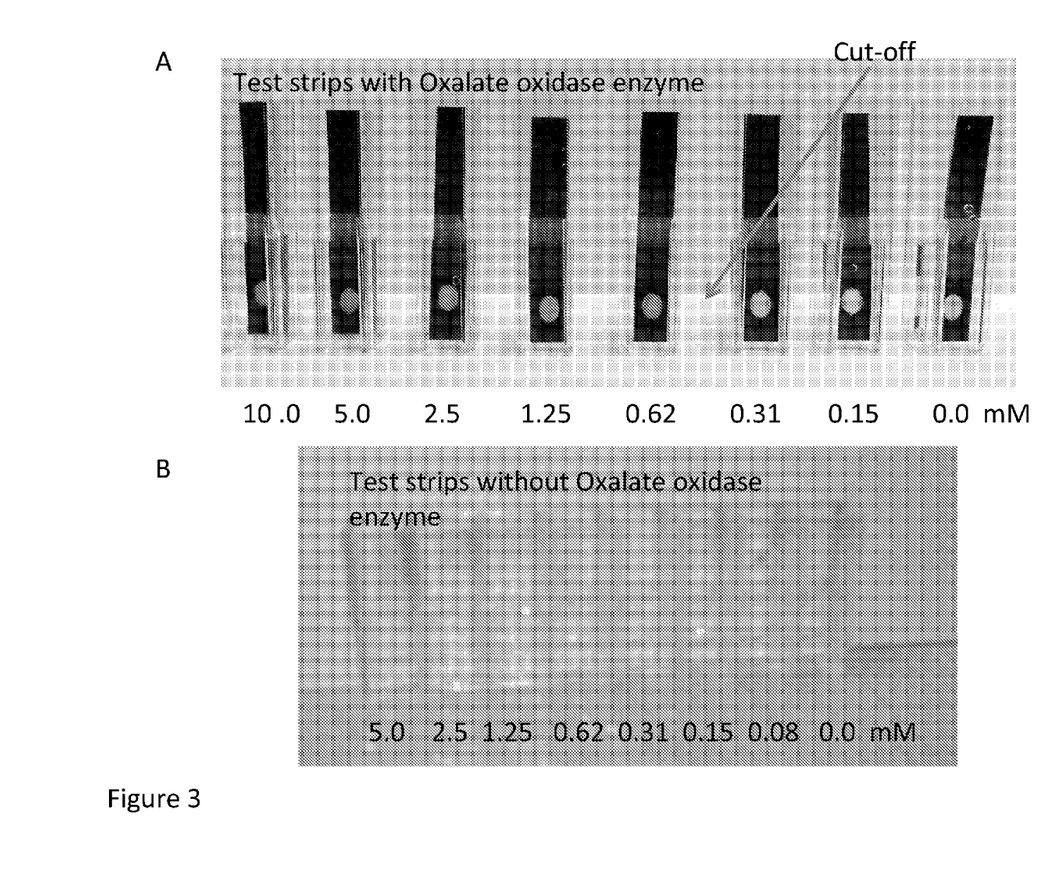
FIG. 3A depicts the detection of oxalate in solution using test device strips imbedded with oxalate oxidase enzyme. Test device strips were placed into solutions containing the indicated mM concentrations of oxalate for 45 seconds.
FIG. 3B depicts no reaction of oxalate solutions in the absence of oxalate oxidase. As a control, test device strips lacking oxalate oxidase were placed into solutions containing the indicated mM concentrations of oxalate for 45 seconds.
FIG. 3C depicts color development in oxalate solutions exposed to test strips imbedded with oxalate oxidase for 1 minute.

Oxalate Test Strips Imbedded with Oxalate Oxidase Enzyme Detected Oxalate in Solution Oxalate test strips were imbedded with oxalate oxidase enzyme. Test strips were placed into solutions containing known concentrations of oxalate for 45 seconds. Oxalate was detected in solution using the test strips (FIG. 3A). The sensitivity of the strips was determined to be between 0.62 and 0.31 mM oxalate. As a control, test device strips lacking oxalate oxidase were placed into solutions containing known concentrations of oxalate. No color reaction was detected for the oxalate solutions in the absence of oxalate oxidase (FIG. 3B). Solutions of oxalate were exposed to test strips imbedded with oxalate oxidase for 1 minute. Color development was observed in oxalate solutions exposed to test strips imbedded with oxalate oxidase for 1 minute (FIG. 3C). Based on the differential between 0.62 and 0.31 mM oxalate solutions, the sensitivity was determined to be between 0.62 and 0.31 mM oxalate. An oxalate concentration >0.5 mM is indicative of hyperoxaluria.

Enzyme activity of specific quantities of the oxalate oxidase enzyme in a constant amount of oxalate were tested. Oxalate test strips were imbedded with varying amounts of oxalate oxidase enzyme. As the amount of oxalate is held constant while the amount of oxalate oxidase is varied, the reactions represent a dilution curve of the enzyme.

Figure 4:
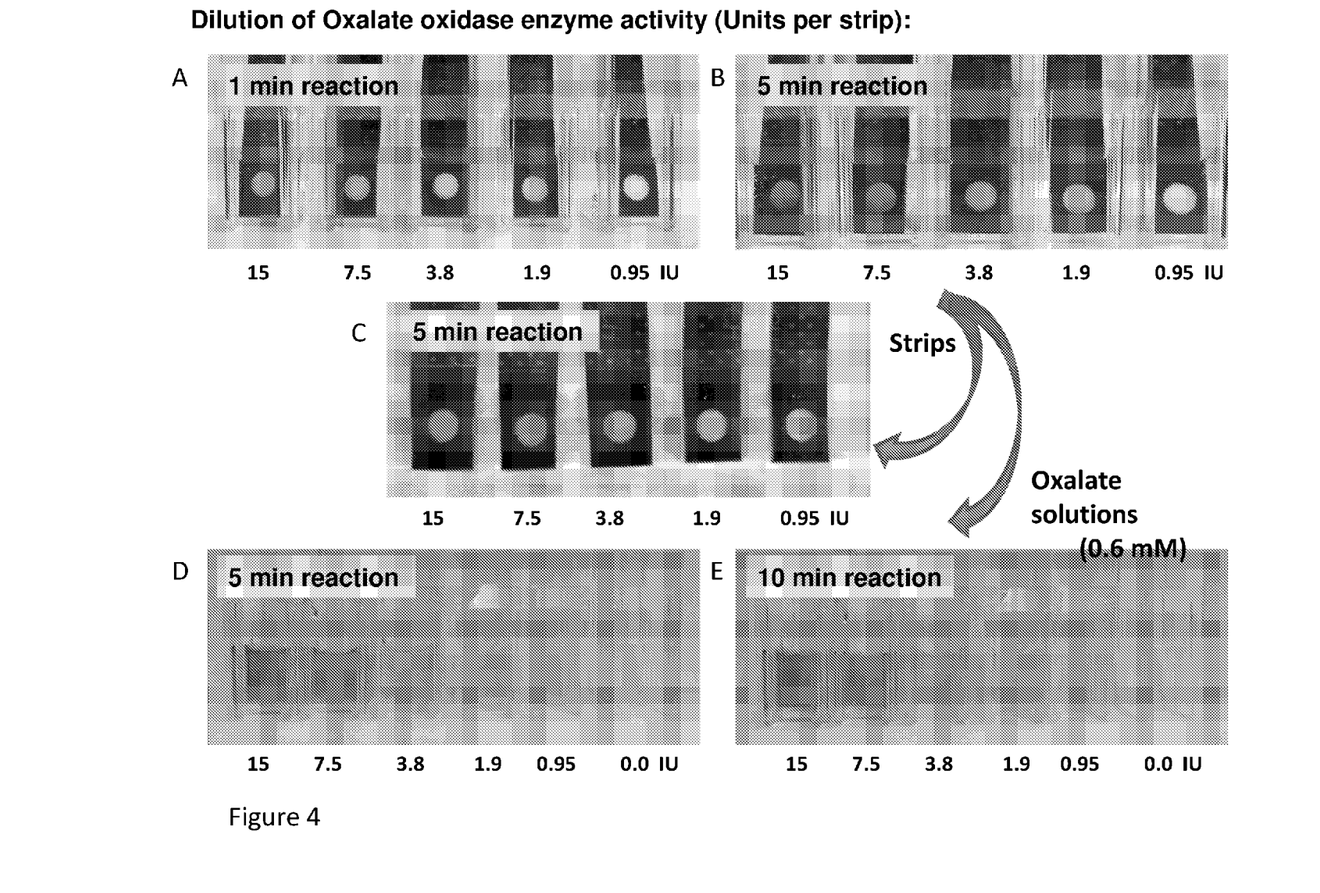
FIG. 4A depicts the detection of 0.6M oxalate in solution after 1 min. using test device strips imbedded with oxalate oxidase enzyme (0.95-15 IU).
FIG. 4B depicts the detection of 0.6M oxalate in solution after 5 min. using test device strips imbedded with oxalate oxidase enzyme (0.95-15 IU).
FIG. 4C depicts the detection of 0.6M oxalate in solution after 5 min. using test device strips imbedded with oxalate oxidase enzyme (0.95-15 IU).
FIG. 4D depicts color development in an oxalate solution (0.6M) exposed to test strips imbedded with oxalate oxidase (0.95-15 IU) for 5 min.
FIG. 4E depicts color development in an oxalate solution (0.6M) exposed to test strips imbedded with oxalate oxidase (0.95-15 IU) for 10 min.
FIG. 4F depicts color development in an oxalate solution (0.6M) exposed to test strips imbedded with oxalate oxidase (0.95-15 IU) for 5 min.
FIG. 4G depicts color development in an oxalate solution (1.25 M) exposed to test strips imbedded with oxalate oxidase (0.95-15 IU) for 3 min.

Oxalate test strips were imbedded with 0.95-15 IU oxalate oxidase enzyme/strip. The strips were used to test an oxalate solution (0.62 mM oxalate) and the reactions observed at 1 min. and 5 min. time points. At these time points, oxalate test strips having at least 3.8 IU oxalate oxidase detected oxalate (0.62 mM) in solution (FIGS. 2A-2C). Color development was also observed in the oxalate solution exposed to the test strips after 5 min. and 10 min. At these time points, oxalate test strips having at least 1.9 IU oxalate oxidase changed color, thus, detecting oxalate (0.62 mM) in solution. (FIGS. 4D and 4E). Thus, in this study oxalate strips having at least 1.9 IU oxalate oxidase are useful for detecting oxalate. Once the activity of an enzyme preparation is determined, the amount of enzyme preparation to be applied to each test strip is determined.

Reactions with the test strips on 0.6 mM and 1.25 mM oxalate solutions were compared. Consistent with other results, oxalate test strips having at least 1.9 IU oxalate oxidase detected 0.62 mM oxalate in solution, as shown by color development after about 5 min. (FIG. 4F). Oxalate test strips having at least 0.95 IU oxalate oxidase detected 1.25 mM oxalate in solution after about 3 min. (FIG. 4G).

Thus, oxalate test strips imbedded with oxalate oxidase enzyme provide a rapid, inexpensive, sensitive, and highly accurate assay for detecting oxalate that can be used at point of care (e.g., at home).

Example 2

Point-of-Care Oxalate Test Kit

The invention provides a point-of-care test kit for monitoring oxalate levels in a biological sample (e.g., urine). In certain embodiments, the contents of the oxalate test kit contains one or more reaction vials, one or more plastic squeeze droppers (e.g., two); one or more plastic bottles of sterile water; and an instruction sheet, including a color chart. The reaction vials contain an oxalate enzyme system in powder form that produces a color change for monitoring oxalate in solution. The powder formulation comprises oxalate oxalase enzyme (5.0 IU activity), EDTA (0.0010 mM), DMAB (0.0050 mM), and MBTH (0.0005 mM). Depending on the number of required measurements, the kit may contain more than one of each of the above items. Optionally, the kit contains urine specimen collection cups.

At time of testing for oxalate levels in a urine sample, 1.0 ml of $H_2O$ is dispensed into a single reaction vial using the dropper provided. By squeezing the dropper, water is added up to an indicated marker line. The powder is dissolved by gentle shaking. This solution should be active for 1 hr. A mid-stream urine specimen is collected. Using a dropper provided, 1.0 ml of urine is dispensed into the reaction vial, tightly capped, and shaken. After allowing the vial sit for 3-5 minutes, the color of the solution is compared to the color chart provided. A reading less than 0.50 mg/ml is considered normal for both male and females.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A test device for detecting oxalate in a liquid sample of a subject, the device comprising oxalate decarboxylase, and an indicator system that provides a detectable reaction product in response to formate production, wherein the device detects oxalate in the liquid sample within 10 minutes of obtaining the liquid sample from the subject.

2. The test device of claim 1, wherein the indicator system comprises phenazine methosulfate (PMS) and iononitro tetrazolium (INT).

3. The test device of claim 1, wherein the device comprises a liquid permeable substrate.

4. The test device of claim 3, wherein the liquid permeable substrate is in the form of a strip.

5. The test device of claim 1, wherein the device comprises the oxalate oxidase or oxalate decarboxylase and the indicator system in powder form, and the device is suitable for containing a liquid.

6. The test device of claim 5, wherein the device is in the form of a cuvette or other clear liquid container.

7. A test device for detecting oxalate in a liquid sample of a subject, the device comprising a liquid permeable material defining the following portions in capillary communication:
 a) a site for application of a liquid sample, comprising a liquid permeable medium;
 b) a second portion comprising a liquid permeable medium; and
 c) a third portion that is the site for detecting the presence of oxalate at the test site, the third portion comprising a liquid permeable medium having an enzyme system having oxalate specific enzyme activity fixed to the medium at the test site, the enzyme system comprising oxalate specific enzyme, a substance which reacts with a reaction product of the oxalate specific enzyme, and an indicator material which reacts in the presence of the reaction product and changes color, wherein the device detects oxalate in the liquid sample within 10 minutes of obtaining the liquid sample from the subject.

8. The test device of claim 7, wherein the enzyme system has oxalate decarboxylase activity, the enzyme system comprising an oxalate decarboxylase, a substance having formate dehydrogenase activity, and an indicator material which is reduced in the presence of formate and changes color.

9. The test device of claim 7, further comprising a fourth portion that acts as a wick, the fourth portion comprising sorbent material.

10. The test device of claim 7, wherein the second portion comprises an agent that alters the composition of the liquid as it contacts the second portion.

11. The test device of claim 10, wherein the second portion comprises a liquid permeable material that acts as a filter to remove particulates.

12. The test device of claim 10, wherein the second portion comprises an agent that alters a physical characteristic of a liquid sample flowing through the second portion.

13. The test device of claim 12, wherein the agent is a buffer, a surfactant, or a salt.

14. The test device of claim 13, wherein the altered physical characteristic is pH, salt concentration, or buffering capacity of the liquid sample.

15. The test device of claim 7, wherein the device further comprises a fourth portion comprising absorbent material that facilitates the flow of liquid through the device.

16. The test device of claim 7, wherein the liquid sample is blood, urine, or saliva.

17. A method for detecting an analyte in a liquid sample, the method comprising:
   a) applying a liquid sample to the device of claim 1; and
   b) detecting presence or absence of oxalate at a test site, wherein the presence of a detectable reaction product or color change at the test site identifies the presence of oxalate in the sample and the absence of color change at the test site identifies the absence of the oxalate in the sample.

18. A kit comprising the test device of claim 1, a reaction mix, the reaction mix comprising an enzyme system having oxalate specific enzyme activity, the enzyme system comprising oxalate specific enzyme, a substance which reacts with a reaction product of the oxalate specific enzyme, and an indicator which reacts in the presence of the reaction product and changes color.

19. The kit of claim 18, wherein the enzyme system has oxalate decarboxylase activity, the enzyme system comprising an oxalate decarboxylase, a substance having formate dehydrogenase activity, and an indicator which is reduced in the presence of formate and changes color.

20. The kit of claim 19, comprising one or more of a powdered reaction mix, a reconstitution buffer, and dispensing pipette.

21. The test device of claim 1, wherein the test device detects oxalate in the liquid sample within 5 minutes of obtaining the liquid sample from the subject.

22. The test device of claim 1, wherein the test device detects oxalate in the liquid sample within 3 minutes of obtaining the liquid sample from the subject.

23. The test device of claim 1, wherein the test device detects oxalate in the liquid sample within 1 minute of obtaining the liquid sample from the subject.

24. The test device of claim 1, wherein the test device detects oxalate in the liquid sample at a point of care for the subject.

* * * * *

UNITED STATES PATENT AND TRADEMARK OFFICE
CERTIFICATE OF CORRECTION

| | | |
|---|---|---|
| PATENT NO. | : 9,045,794 B2 | Page 1 of 1 |
| APPLICATION NO. | : 13/984251 | |
| DATED | : June 2, 2015 | |
| INVENTOR(S) | : Ammon B. Peck et al. | |

It is certified that error appears in the above-identified patent and that said Letters Patent is hereby corrected as shown below:

In the Specification,

Column 1, line 13

Applicants request the government support statement identified below be inserted in this patent after the "CROSS REFERENCE TO RELATED APPLICATIONS" section:

-- STATEMENT OF GOVERNMENT SUPPORT
This invention was made with United States government support under NIH Grant No. DK061666 awarded by the National Institutes of Health. The United States government has certain rights in this invention. --

Signed and Sealed this
First Day of March, 2016

Michelle K. Lee
*Director of the United States Patent and Trademark Office*